US00PP36205P2

(12) United States Plant Patent
MacKenzie

(10) Patent No.: US PP36,205 P2
(45) Date of Patent: Oct. 15, 2024

(54) ***PANICUM* PLANT NAMED 'Nonlufht'**

(50) Latin Name: *Panicum virgatum*
Varietal Denomination: Nonlufht

(71) Applicant: Hortech, Inc., Nunica, MI (US)

(72) Inventor: David MacKenzie, Nunica, MI (US)

(73) Assignee: HORTECH, INC., Nunica, MI (US)

( * ) Notice: Subject to any disclaimer, the term of this patent is extended or adjusted under 35 U.S.C. 154(b) by 0 days.

(21) Appl. No.: 18/421,203

(22) Filed: Jan. 24, 2024

(51) Int. Cl.
*A01H 5/12* (2018.01)
*A01H 6/46* (2018.01)

(52) U.S. Cl.
USPC ..... Plt./384
CPC ..... *A01H 6/4642* (2018.05)

(58) Field of Classification Search
USPC ..... Plt./384
CPC ..... A01H 5/12
See application file for complete search history.

*Primary Examiner* — Kent L Bell
(74) *Attorney, Agent, or Firm* — Penny J. Aguirre

(57) ABSTRACT

A new cultivar of *Panicum* plant named 'Nonlufht' that is characterized by its plant height of 1.98 m (to top of inflorescence) and plant width of 1.83 m (at the widest point), its vase-shape with arching foliage at the top with a tight base, its green foliage, and its silver flowers.

1 Drawing Sheet

Botanical classification: *Panicum virgatum.*
Varietal denomination: 'Nonlufht'.

BACKGROUND OF THE INVENTION

The present invention relates to a new and distinct cultivar of *Panicum virgatum* and will be referred to hereafter by its cultivar name, 'Nonlufht'. 'Nonlufht' represents a new cultivar of switchgrass, an ornamental grass grown for landscape use.

The new cultivar of *Panicum* was derived from an ongoing controlled breeding program conducted by the Inventor in Nunica, Michigan. The goals of the breeding program include developing new cultivars of *Panicum* with novel ornamental traits that include strong stature, compact habits, and unique foliage or flower colors.

'Nonlufht' originated as a seedling that arose from open pollination in a production field containing numerous cultivars and proprietary seedlings of *Panicum virgatum* varieties at the Inventor's nursery in September of 2019. The collected seeds were pooled prior to planting in an evaluation field plot and therefore the parentage is unknown. Nonlufht' was selected as a single unique plant in September of 2021 from amongst the resulting seedlings.

Asexual propagation of the new cultivar was first accomplished by the Inventor by rhizome division in Nunica, Michigan in September of 2021. Asexual propagation by division and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Nonlufht' as a unique cultivar of *Panicum.*

1. 'Nonlufht' exhibits a plant height of 1.98 m (to top of inflorescence) and plant width of 1.83 m (at the widest point).
2. 'Nonlufht' exhibits a vase-shape with arching foliage at the top with a tight base.
3. 'Nonlufht' exhibits green foliage.
4. 'Nonlufht' exhibits silver flowers.

'Nonlufht' can be most closely compared to *Panicum* cultivars, 'Northwind' (not patented), and 'Cloud Nine' (not patented). 'Northwind' is similar to 'Nonlufht' in having an upright plant habit and green foliage. 'Northwind' differs from 'Nonlufht' in having a less tight plant base and less broad in width, slightly less tall in height, and amber colored flowers. 'Cloud Nine' is similar to 'Nonlufht' in having a vase-shaped plant habit. 'Cloud Nine' differs from 'Nonlufht' in having a wider base that is not as tight, a taller plant height, and foliage that is blue-green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include a website listing by Hortech.

BRIEF DESCRIPTION OF THE DRAWING

The accompanying color photograph illustrates the overall appearance and distinct characteristics of the new *Panicum*. The photograph was taken of a 5-year-old plant of 'Nonlufht' as grown outdoors in a trial garden in Nunica, Michigan. The photograph provides a side view of 'Nonlufht' in bloom. The colors in the photograph are as close as possible with the photographic and printing technology utilized and the color values cited in the Detailed Botanical Description accurately describe the colors of the new *Panicum*.

DETAILED BOTANICAL DESCRIPTION OF THE PLANT

The following is a detailed description of five-year-old plants of the new cultivar as grown outdoors in a trial garden in Nunica, Michigan. The phenotype of the new cultivar may vary with variations in environmental, climatic, and cultural conditions, as it has not been tested under all possible environmental conditions. The color determination is in accordance with the 1986 and 2007 RHS Colour Chart of The Royal Horticultural Society, London, England, except where general color terms of ordinary dictionary significance are used.

General Description:

*Blooming period*.—From August until October in Michigan.

*Plant type*.—Herbaceous perennial grass.

*Plant habit*.—Upright, vase-shaped with a tight base, nonlodging clump of foliage with upright flowering spikes.

*Height and spread*.—An average of 1.98 m in height (including inflorescences) and 1.83 m (at the widest point) in spread as grown in the landscape for 5 years.

*Hardiness zone*.—At least in U.S.D.A. zones 4 to 9.

*Diseases*.—Good resistance to rust (caused by *Puccinia emaculata*) has been observed.

*Root description*.—Fibrous and fine, deeply rooted, a blend between 159B and 158C in color.

*Propagation*.—Rhizome division and tissue culture.

*Rhizomes*.—An average of 3 cm in length and 0.5 cm width and 155A in color.

*Growth rate*.—Moderate for a *Panicum*.

*Time required for root development*.—From 2-inch wide divisions; up to 4 weeks for root initiation with a fully rooted plant in a 3.5-inch container produced in an average of 6 weeks.

Culm (stem) description:

*General*.—Cylindrical, hollow pith, thin but strong, held erect.

*Culm number*.—An average of 8 in an 8-cm container, forming a tight clump.

*Culm color*.—A blend between 138A and 138B in summer, 162A with base 161B to 161C in winter, ranges from 15.2 cm to 17.8 cm of exposed area between leaf nodes.

*Culm size*.—An average of 6.4 mm in diameter and 1.2 m in height from the base to the base of the peduncle.

*Culm surface*.—Glabrous, smooth, and slightly striate.

*Internode length*.—An average of 16.5 cm.

Foliage description:

*Leaf shape*.—Narrowly lanceolate.

*Leaf division*.—Simple.

*Leaf margin*.—Entire, scaberulous.

*Leaf base*.—Sheathed to base of the node.

*Leaf venation*.—Parallel, not distinguishable in color from leaf coloration.

*Leaf width*.—An average of 1.3 cm at widest section.

*Leaf length*.—Blade; an average of 66 cm, sheathed portion; an average of 12.7 cm.

*Leaves per culm*.—An average of 7 on flowering culms.

*Leaf color*.—Upper and lower surfaces 137B.

*Leaf surface*.—Glabrous, dull, and slightly striate on both surfaces.

*Ligule*.—An average of 3.2 mm in height and 6.4 mm in width, color on both surfaces; 157C at the top, covered in fine hairs on the on inner surface that protrude from the top, NN155C in color.

Flower Description:

*Inflorescence type*.—Dense, spreading panicle at terminus of stem, symmetrical, typically 5-flowered spikelet with lower spikelet male and upper spikelet hermaphroditic.

*Inflorescence color*.—Overall color of the raceme is 138C in early summer, maturing to 61A, turns to 161A in the late fall.

*Inflorescence size*.—An average of 45.7 cm in length and 22.9 cm in width.

*Inflorescence arrangement*.—Upright.

*Spikelet description*.—An average of 400 per panicle, oval to elliptic in shape, an average of 6.4 mm in length and 3.2 mm in width, awn present; an average of 0.5 mm in length and 61A in color, lower glume; an average of 4 mm in length and 1 mm in width, upper glume and lower lemma; an average of 4.5 cm in length and 1mm width, color; glumes and lemma upper and lower surface 139D suffused with 60C near the base, palea; an average of 1.5 mm in length and 0 .5 mm in width, translucent and glossy, color of upper and lower surface a blend between 155C and 157D , glumes, lemma, and palea are oval to elliptic in shape and convex with all surfaces glabrous and smooth.

*Rachis*.—An average of 7.6 cm in length from last leaf, raceme portion; an average of 27 cm in length and 1 mm in width, glabrous and smooth surface, 138C in color, lateral branches (peduncle-like); an average of 14, about 0.2 mm in width and an average of 18 cm in length (shortest at terminus), 138B in color, glabrous surface, pedicel; an average of 5 mm in length and 0.2 mm in width, very fine and wiry, 138B in color, glabrous surface.

*Androecium*.—Anthers; 3, an average of 3.5 mm in length and 1.5 mm in width, 172A in color, basifixed on very fine, translucent filament, pollen; moderate in quantity and 162C in color.

Reproductive organs:

*Gynoecium*.—Pistil; 1, 2 plumose stigmas on short, fine styles adnate to ovary, stigma N79B to N79C in color, an average of 1.25 mm in length and 0.89 mm in width, ovary; 1-locular, superior, an average of 3.1 mm in length and 1.15 mm in with, 149D in color.

It is claimed:

1. A new and distinct cultivar of *Panicum* plant named 'Nonlufht' as herein illustrated and described.

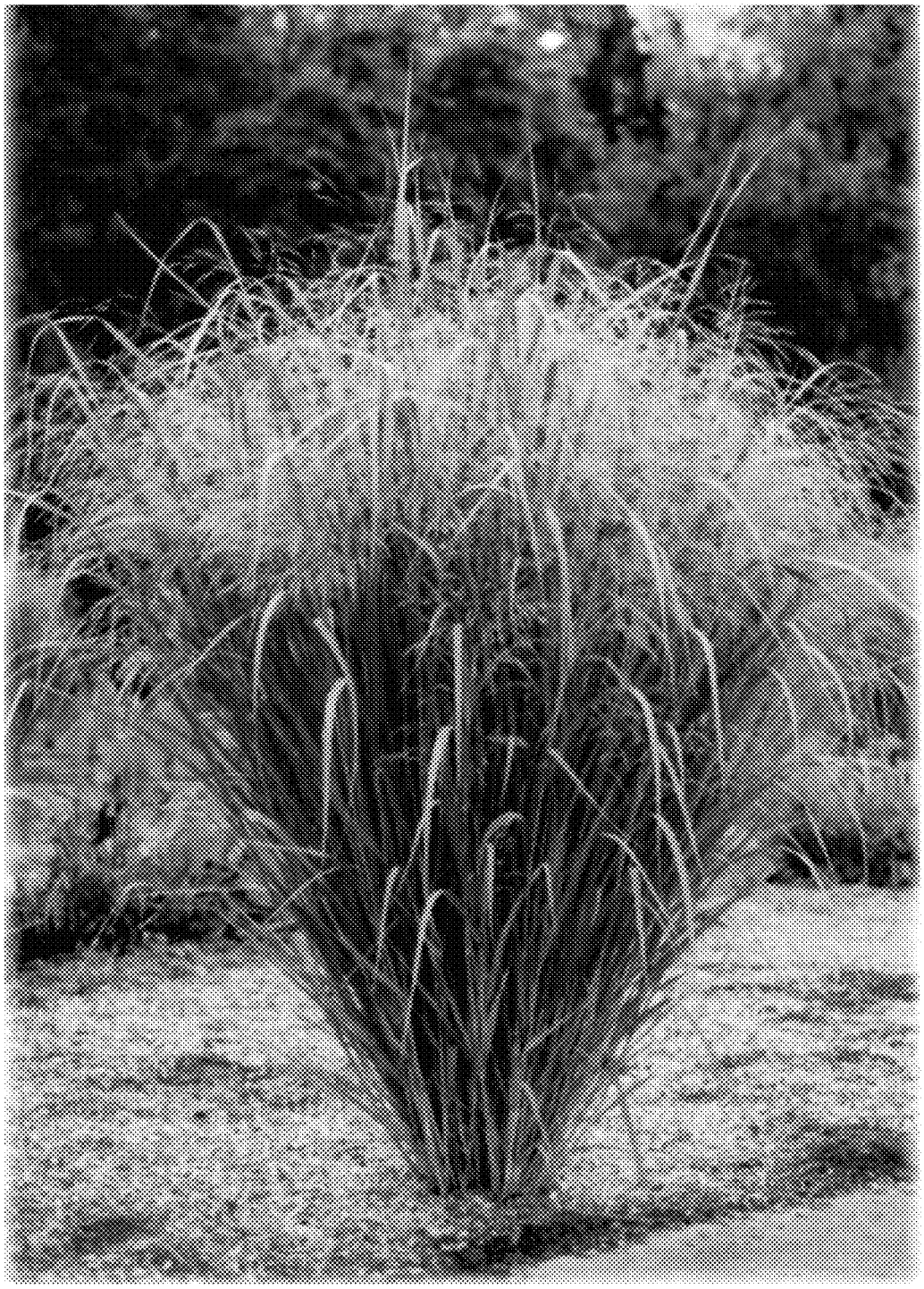

* * * * *